United States Patent [19]

Moore

[11] 4,371,688
[45] Feb. 1, 1983

[54] SUBSTITUTED CYCLOHEXANE-1,2-DICARBOXYLIC ANHYDRIDES AND EPOXY RESINS CONTAINING SAME

[75] Inventor: Patrick D. Moore, Spartanburg, S.C.

[73] Assignee: Milliken Research Corporation, Spartanburg, S.C.

[21] Appl. No.: 323,142

[22] Filed: Nov. 19, 1981

Related U.S. Application Data

[63] Continuation-in-part of Ser. No. 180,300, Aug. 22, 1980, abandoned.

[51] Int. Cl.³ .............................................. C08G 59/42
[52] U.S. Cl. .................................... 528/112; 525/507; 528/115; 518/361; 528/365; 549/240
[58] Field of Search .......................... 260/346.3, 346.6; 252/182; 528/112, 115, 361, 365

[56] References Cited

U.S. PATENT DOCUMENTS

| | | | |
|---|---|---|---|
| 3,078,279 | 2/1963 | McCracken et al. | 260/346.3 |
| 3,269,974 | 8/1966 | Childs | 260/37 |
| 3,272,843 | 9/1966 | Spatz et al. | 528/112 X |
| 3,324,081 | 6/1967 | Barie et al. | 260/47 |
| 3,499,007 | 3/1970 | von Brachel et al. | 528/112 X |
| 3,600,384 | 8/1971 | Moltz | 528/112 X |
| 3,772,228 | 11/1973 | Allen | 260/21 |
| 4,074,036 | 2/1978 | Tuller et al. | 528/112 X |
| 4,158,090 | 6/1979 | Sabourin et al. | 528/92 |
| 4,271,079 | 6/1981 | Maeda et al. | 260/346.3 |

OTHER PUBLICATIONS

Samejima, "Cyclohexenedicarboxylic Acid Anhydrides", Chemical Abstracts 83, 27702f (1975).

*Primary Examiner*—Earl A. Nielsen
*Attorney, Agent, or Firm*—H. William Petry; Terry T. Moyer

[57] ABSTRACT

In accordance with the present invention, there is provided a substituted cyclohexane-1,2-dicarboxylic anhydride (CHDA) having the structural formula:

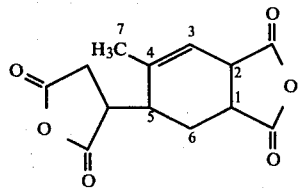

16 Claims, No Drawings

SUBSTITUTED CYCLOHEXANE-1,2-DICARBOXYLIC ANHYDRIDES AND EPOXY RESINS CONTAINING SAME

This application is a continuation-in-part of copending prior application Ser. No. 180,300, filed Aug. 22, 1980, and now abandoned.

The present invention relates to substituted cyclohexane-1,2-dicarboxylic anhydrides (hereinafter CHDA). More particularly, the present invention relates to epoxy curing agents of a polyanhydride type and to high-performance, cured polyepoxides containing polyanhydride curing agents.

Several aromatic polyanhydrides have been developed for use as epoxy curing agents. (As used herein, the term "polyanhydride" is defined to include compounds containing two or more anhydride moieties.) In general because of the number of reactive sites present on the molecule, e.g., four functional groups for a dianhydride, six for a trianhydride, etc., such polyanhydrides may be used to provide highly crosslinked epoxy resins which at high, continuous operating temperature may retain their electrical and physical properties and provide excellent resistance to chemicals and solvents. For instance, as compared to monoanhydride-cured epoxy resin systems which may have relatively low heat distortion temperatures (HDT) of, for instance, 150° C. or less, polyanhydride-cured systems in general typically provide heat distortion temperatures of 200° C. or greater, which may be highly desirable in certain applications.

Aromatic polyanhydrides useful as epoxy hardening agents which are presently known include pyromellitic dianhydride (PMDA), 3,3',4,4' benzophenone tetracarboxylic dianhydride (BTDA), and biphenyl tetracarboxylic dianhydride (BPDA). While these known polyanhydrides have had a fair amount of commercial success, they typically are characterized by several disadvantages that have limited their achievement of the full commercial potential for these types of compounds. For instance, their relatively high melting points, e.g., 286° C. for PMDA, 228° C. for BTDA, and 199° C. for BPDA, has made processing in epoxy resin systems difficult.

Another key problem encountered with known aromatic polyanhydrides is their relatively poor solubility characteristics in epoxy resins. For instance, both PMDA and BTDA must be heated to about 200° C. in order for them to be dissolved in certain epoxy systems, such as the Epon 828 system, a product of Shell Chemical Company. Furthermore, upon cooling they may separate from the resin solution. Their pot life at solution temperatures is also relatively short, typically less than about three minutes for PMDA and BTDA. Even with regard to BPDA, heating to a temperature of about 165° C. or higher is required to form a homogeneous solution of the polyanhydride in Shell's Epon 828 epoxy system, and its pot life is also relatively short.

Another significant deficiency of the known aromatic polyanhydrides resides in their performance in filled epoxy systems. For instance, as disclosed in U.S. Pat. Nos. 3,269,974 and 3,772,228 (both of which are incorporated by reference), typical filled resin system may be prepared by adding the finely divided powdered polyanhydride to the desired powdered epoxy resin at room temperature, followed by the addition of the desired filler. The resultant composition may be ground up into a fine powder. The particular composition may then be used immediately or it may be stored for periods of up to about six months or even longer. During subsequent curing at curing temperatures where the epoxy goes into the liquid phase, the prior art polyanhydrides ordinarily do not dissolve in the epoxy prior to the attainment of rapid reaction temperature, but remain in the liquid epoxy as a suspended solid. Consequently, the overall amount of filler which may be added is limited due to the limit on the amount of suspended solids which the liquid system can effectively accommodate. Of course, the more filler that can be added to the resin system, the lower the cost of the overall system; and it would, accordingly, be desirable to provide a polyanhydride curing agent that does not remain in the liquid resin system as a suspended solid, thereby limiting the amount of filler that can be added, but rather goes into the liquid phase at normal processing temperatures so that the filler is the only suspended solid in the liquid system.

Accordingly, the new polyanhydride compounds of the present invention typically may be characterized as possessing the known advantages associated with polyanhydride curing agents while minimizing or eliminating the known disadvantages of such systems. Thus, more temperature-stable epoxy resins may be provided than are possible when monoanhydrides are used alone to cure epoxy resins. The cured epoxy resins of the present invention may have high heat distortion temperatures, e.g., in excess of 260° C., and they may impart other improved physical properties to the cured epoxy resin product. The new curing agents may also be easily processed in epoxy resin systems. The new polyanhydrides of the invention typically have relatively low melting points, e.g., typically less than about 115° C., preferably even less than about 90° C.

These new compounds, furthermore, may be dissolved more easily in epoxy resin systems such as Shell's Epon 828 than heretofore has been possible with known polyanhydride epoxy curing agents. Frequently dissolution in epoxy resin systems may be possible at temperatures of 130° C. or even less. Also, substantially longer pot life compared to known polyanhydrides may be achieved for epoxy resin systems employing the polyanhydride curing agents of the present invention.

The present invention also provides improved filled epoxy systems having a lower cost due to the increased level of filler which may be provided in the filled epoxy resin product. Such increased amount of filler may be provided because the new polyanhydride compounds of the present invention may be substantially or even completely dissolved in the liquid epoxy resin so that the amount of filler employed is not limited by excessive amounts of suspended solid particles of polyanhydride in the liquid epoxy resin. The present invention also provides improved epoxy curing agent mixtures where the polyanhydrides of the present invention are mixed with the known monoanhydride curing agents.

In accordance with the present invention, there are provided certain polyanhydrides. The polyanhydrides of the invention may be described as substituted cyclohexane-1,2-dicarboxylic anhydrides (CHDA) having the structural formula:

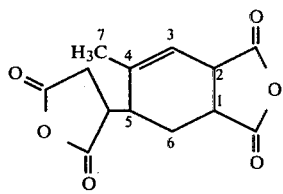

While a polyanhydride having the above structural formula is the predominant or sole component of the polyanhydride product of the present invention, it should be recognized that the products of the present invention may not contain only one isomer but may contain in addition to the polyanhydride compound I set forth above as the predominant component a minor amount, e.g., from about 5 to about 45 parts, preferably from about 15 to about 30 parts per 50 parts by weight of polyanhydride compound I, of an isomeric compound having the ethylenic unsaturation in the 4-7 position. Such compounds may be represented by the formula:

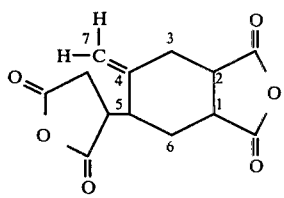

The present invention also relates to compositions containing one or more known curing agents for epoxy resins, e.g., a monoanhydride curing agent and the substituted CHDA compound of the present invention. Such monoanhydride curing agents may be selected from a wide range of compounds, such as, for instance, succinic, tetrahydrophthalic, methylnadic, methyltetrahydrophthalic, phthalic, alkenylsuccinic, alkylsuccinic, hexahydrophthalic, methylhexahydrophthalic anhydrides. For instance, such compositions may include relative proportions of monoanhydride to CHDA compound varying over a wide range depending upon the properties desired in the cured product. Such compositions may be particularly useful in the preparation of cured epoxide resins having improved thermal and electrical properties as evidenced by the following examples.

The novel substituted CHDA compound of the present invention may be prepared by simply reacting a suitable ethylenically unsaturated anhydride, e.g., maleic anhydride, with a suitable cycloaliphatic ethylenically unsaturated anhydride such as 4-methyl tetrahydrophthalic anhydride (MTHPA). In general, from about 15 parts to about 75 parts, preferably from about 45 parts to 60 parts by weight of maleic anhydride may be reacted with 100 parts of 4-methyl tetrahydrophthalic anhydride. The cycloaliphatic ethylenically unsaturated anhydride may be prepared conveniently and inexpensively from maleic anhydride and isoprene, i.e., 2-methyl-1,3-butadiene. The product compound may then be prepared by heating the reactants to a temperature of from about 150° C. to 300° C., preferably about 215° C., and maintained at that temperature for from about 0.25 to about 48 hours, preferably about 4–12 hours. The resulting reaction mixture may be suitable for use as is, or if isolation of the polyanhydride is desired, the reaction mixture may be subjected to vacuum distillation to recover unreacted starting material as a boiling fraction. The product may remain as a residue in the distillation apparatus and it may be cooled to form a solid which may be pulverized to form a powder.

Determination of the major specific isomers present in a given product may be made using a combination of reaction theory and NMR analysis. Based upon the best available scientific evidence, a typical product made according to the above preparation process may include a mixture of compounds, the predominant component of which has the following structure:

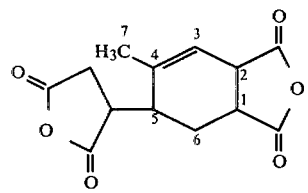

The novel polyanhydride of the present invention may have a wide spectrum of utilities. For instance, one particularly important use for the novel compound of the present invention is its use as epoxy curing agents for polyepoxides.

The polyepoxides that can be cured at elevated temperatures using the polyanhydride compound or compositions containing such compound as herein described are those polyepoxides possessing more than about 1 epoxy group. These groups may be terminal groups, or they may be in an internal position. However, especially desirable results can be obtained when the epoxy groups are terminal. The polyepoxides may be saturated or unsaturated, aliphatic, cycloaliphatic, aromatic or heterocyclic, and may be substituted such as with hydroxyl groups, ether radicals, and the like. Further, the polyepoxides, and their preparation, are well-known in the art.

The epoxy resin system may be either a liquid or solid epoxy resin system. Typical liquid systems may include the diglycidyl ethers of Bisphenol A (herein DGEBA) and cycloaliphatic types. Typical solid systems include DGEBA, cycloaliphatic, and novolac types. Liquid and solid resins may be mixed to impart specific properties to the final resin, which may be cured with the polyanhydride of the present invention. Such monoanhydrides may include, for instance, maleic anhydride, nadic methyl anhydride, and hexahydrophthalic anhydride, methyl tetrahydrophthalic anhydride, etc. Such mixed anhydride systems provide novel epoxy curing compositions that may have improved properties.

The curing of the polyepoxides with the above-described polyanhydride curing agent of the present invention may be accomplished by simply mixing the two components together and then heating them. Reaction between the two components occurs very slowly at room temperature which is desirable, for instance, when the two component system is to be stored for rather long periods of time of six months or even longer. Then if the mixture is heated to a temperature of at least about b 100° C. for from about 1 to about 5 hours, curing may be accomplished. Thereafter post-curing the reaction product for an additional period of time from about 4 to about 18 hours at a temperature of from about 190° C. to about 200° C. may be performed. With a small casting, curing of the reaction mixture can be obtained by heating the reaction mixture for about 2 hours at a temperature of from about 100° C. to about 120° C. and thereafter post-curing the reaction product at a temperature of from about 190° C. to about 200° C. for an additional 4-18 hours or so.

In curing polyepoxides it is generally desirable that the polyepoxide be in a mobile condition when the curing agent is added to ensure uniform mixing. If the polyepoxide is extremely viscous or solid at room or casting temperature, the polyepoxide may be heated to reduce the viscosity or a volatile liquid solvent may be added which can escape from the polyepoxide composition containing the polyanhydride curing agent by evaporation before and/or during the curing of such polyepoxide composition. Typical of such volatile liquid solvents are ketones, such as acetone, methylethyl ketone and the like, esters, such as ethyl acetate, butyl acetate and the like, and chlorinated hydrocarbons, such as chloroform. Use of solvents which may react with the polyanhydride of the invention should be avoided.

The cured epoxy resins that are also within the scope of the present invention and that may be made using the polyanhydride of the invention or its mixtures with monoanhydrides may find applications as coatings, molding powders, electrical insulating coatings, structural laminates, powder coatings, filament wound pipe, and specialty adhesives, among others.

In addition to the use of the polyanhydride of the present invention as an epoxy curing agent, many other uses can readily be envisioned by those skilled in the art. Such applications may include, for instance, additions to: polyesters (ranging from unsaturated to alkyd), elastomers for polyurethanes, alcohols for solvents and lubricants, and diamines for polyamides and polyimides.

In order to more fully describe the preparation and use of the novel compound of the present invention, the following examples are given. However, such examples are presented for illustration only and are not to be construed as unduly limiting the scope of the present invention. Unless otherwise indicated, all parts and/or percentages given in these examples are by weight. In the examples, Examples I, II and III illustrate the preparation of the novel polyanhydride of the invention. Examples IV and V illustrate the utility of the novel polyanhydride as an epoxy curing agent.

EXAMPLE I

One hundred ninety-six parts of maleic anhydride and 398 parts of 4-methyl tetrahydrophthalic anhydride (derived from isoprene and maleic anhydride) were added to a one-liter, electrically heated, stirred stainless steel Autoclave Engineering reactor. The reactor was sealed, flushed with nitrogen gas, and heated to 375° F. (192° C.). After the reaction temperature stabilized (0.5–1.0 hour), the temperature was raised to 400° F. (205° C.) and maintained at that temperature for five hours. Cooling was applied as needed to maintain the indicated temperature levels. After the indicated reaction time, the product was cooled and a 319 part sample was transferred warm to a round-bottom flask. The sample was stirred and vacuum-distilled at 2-4 mmHg. One fraction containing unreacted starting material was collected below 170° C. (distillate temperature) (184 parts, 58 percent). The product in the pot was poured onto a metal sheet and after cooling it was broken into pieces and powdered (86 parts, 27 percent). The product melted at 88° C.

Analysis of the product to determine its structure revealed the following:
(1) The Infrared showed strong bands at 1780 and 1860 cm$^{-1}$, characteristic of succinic anhydride groups. Other strong bands were observed at 1230 and 920 cm$^{-1}$.
(2) Gas chromatographic analysis revealed no maleic anhydride and only traces of MTHPA in the product.
(3) The neutralization equivalent of the product was 67-70 mg/meq (66.0 mg/meq theoretical).
(4) CHN analysis 57.27% carbon, 4.55% hydrogen, 38.12% oxygen (59.07, 4.58, and 36.3 theoretical).
(5) The hydrogen NMR shows signals characteristic of terminal double-bond hydrogens

predicted by the proposed "ene" reaction mechanism and absent in both thermal- and acid-catalyzed isomerization of MTHPA.

Based upon the above analysis, the product may be characterized as a mixture of isomers, the predominant component of which is a compound of the following structural formula:

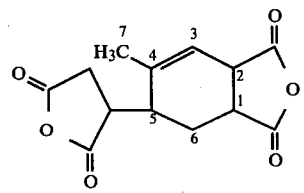

EXAMPLE II

Two hundred seventy-five parts of maleic anhydride and 458 parts of methyl tetrahydrophthalic anyhdride (1.0 molar ratio) were placed in glass pressure bottles, flushed with nitrogen, and sealed. After five hours in an oil bath at 225° C., the samples were cooled, combined, and vacuum-distilled as in Example I. Recovered starting materials equaled 360 parts (49 percent); product equaled 330 parts (45 percent). Using the same methods of analysis detailed in Example I above, it was determined that the product compound was a mixture of isomers with the same structural formula shown for Example I.

EXAMPLE III

Seven hundred fifty parts MTHPA and 300 parts maleic anhydride (1.5 molar ratio) were reacted as in Example II for six hours at 210° C. Removal of unreacted starting materials by vacuum distillation gave 90 parts (8.5 percent) product MP 55°-75° C., neutralization equivalent 68.2 mg/meq. Hydrogen NMR shows vinyl hydrogen signals at 5.95, 5.68, and 5.08 ppm with relative areas of 1, 6, and 12 respectively. This indicates that the product contains in addition to a predominant amount of the 3-4 isomer shown in Example I an isomer having the ethylenically unsaturated group in the 4-7 position of the formula:

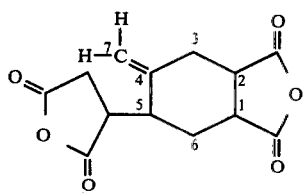

EXAMPLE IV

This example illustrates that the compounds of the present invention may form homogeneous solutions with liquid epoxy resin systems in at least the 25 to 70 parts per hundred parts of resin range. Thus, 24 grams of Epon 828 were placed in a metal beaker and warmed to 130° C. in an oil bath. Fifteen grams of a product were added having a mixture of isomers, the predominant component of which has the following structure:

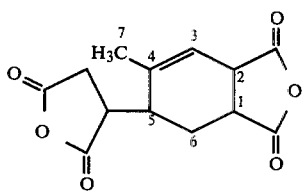

After a few minutes, a dark homogeneous solution occurred. Twenty-five mg (0.1 phr) of DMP-30 was mixed with one gram Epon 828 and then added to the hot solution. Separate samples were cured at 90° C. for 2.5 hours, 120° C. for 1.5 hours, 150° C. for 2 hours, and 200° C. for 12 hours. Tg measurements indicated a transition greater than 200° C. Weight loss versus temperature (air @ 40° C./min) shows a transition beginning near 400° C. and crossing 50 percent weight loss at 490° C., indicating substantial heat resistance.

EXAMPLE V

This example illustrates the improved performance of epoxy resins derived from monoanhydride curing agents when the pure monoanhydride curing agents are replaced by a mixture of monoanhydride curing agent and the polyanhydride product of this invention represented by the following structure:

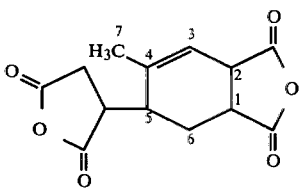

Thus, Milldride 5014 (a product of Milliken Chemical which is a mixture of $C_8$ and $C_9$ cyclic unsaturated monoanhydrides) and the polyanhydride product of this invention shown above were mixed at various levels as shown in column 2 of Table I. The resulting solutions were mixed with Epon 828 and cured by application of heat in the presence of the amount of a tri-benzyl amino catalyst, DMP-30, available from Rohm & Haas. Table I shows the details of the mixtures and the improvement of thermal and electrical properties observed.

TABLE I

| Sample | % Milldride 5014 | % CHDA | Catalyst % | phr of Anhydride | HDT* °C. | Temperature where D**0.02 |
|---|---|---|---|---|---|---|
| 1 | 100 |  | 1 | 79 | 122 | 135 |
| 2 | 90 | 10 | 1 | 77 | 137 | 150 |
| 3 | 80 | 20 | 1 | 75 | 143 | 160 |
| 4 | 0 | 100 | 0 | 40 | 272 | >170° C. |

*Heat Distortion Temperature, ASTM Standard Method No. D-648
**Dissipation Factor ASTM Standard No. D-150

What is claimed is:

1. A substituted CHDA having the structural formula:

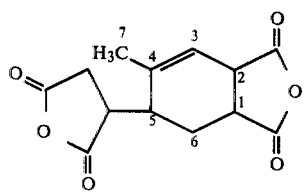

2. A substituted CHDA composition which comprises a predominant amount of a compound of the formula:

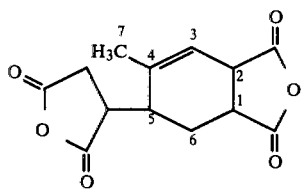

and a minor amount of a compound of the formula:

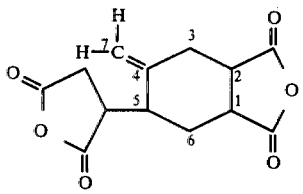

3. An epoxy curing agent composition which comprises a monoanhydride epoxy curing agent, and a substituted CHDA having the structural formula:

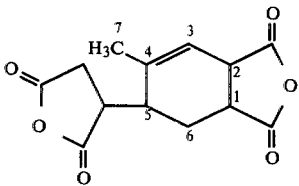

4. A curable epoxy resin composition comprising an epoxy resin and an epoxy resin curing agent, wherein the epoxy resin curing agent is represented by the formula:

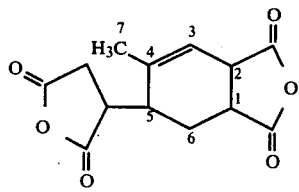

5. The epoxy resin composition of claim 4, wherein said epoxy resin is selected from polyepoxides possessing more than about 1 epoxy group.

6. The epoxy resin composition of claim 4, wherein said epoxy groups are terminal groups.

7. The epoxy resin composition of claim 6, wherein said epoxy resin is a diglycidyl ether of bisphenol.

8. A curable epoxy resin composition which comprises an epoxy resin and an epoxy resin curing agent composition, said composition comprising a monoanhydride epoxy curing agent and a substituted CHDA having the structural formula:

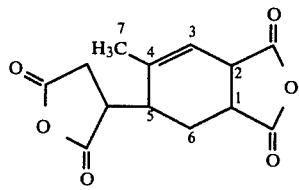

9. The epoxy resin composition of claim 3, wherein said monoanhydride epoxy curing agent is selected from succinic, alkenyl succinic, alkylsuccinic, phthalic, tetrahydrophthalic, hexahydrophthalic, methyltetrahydrophthalic, methylhexahydrophthalic, and methylnadic anhydrides.

10. In a method for curing an epoxy resin composition comprising incorporating an epoxy resin curing agent into an epoxy resin and heating the combination of the epoxy resin and the epoxy curing agent, the improvement which comprises said epoxy resin curing agent being represented by the formula:

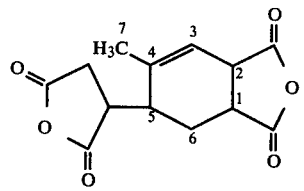

11. A process for preparing a substituted cyclohexane-1,2-dicarboxylic anhydride which comprises reacting 100 parts by weight of 4-methyl tetrahydrophthalic anhydride with from about 15 to about 75 parts by weight of maleic anhydride at a temperature of from about 150° C. to about 300° C. for a period of time sufficient to form substantial amounts of substituted cyclohexane-1,2-dicarboxylic anhydride in a crude reaction product.

12. The process of claim 11, wherein said crude reaction product is subjected to vacuum distillation to recover unreacted starting material, said crude reaction product being suitable for use directly as an epoxy curing agent.

13. The product of the process of claim 11.

14. The product of the process of claim 12.

15. A curable composition comprising an epoxy resin and the product of the process of claim 11.

16. A curable composition comprising an epoxy resin and the product of the process of claim 12.

* * * * *

UNITED STATES PATENT AND TRADEMARK OFFICE
CERTIFICATE OF CORRECTION

PATENT NO. : 4,371,688

DATED : February 1, 1983

INVENTOR(S) : Patrick D. Moore

It is certified that error appears in the above-identified patent and that said Letters Patent is hereby corrected as shown below:

Col. 1, line 64, change "system" to --systems--.

Col. 4, line 63, delete "b" at beginning of line.

Col. 9, line 35 (first line of claim 9) change "3" to --8--.

Signed and Sealed this

Sixteenth Day of September 1986

[SEAL]

Attest:

DONALD J. QUIGG

Attesting Officer

Commissioner of Patents and Trademarks